United States Patent [19]

Doss et al.

[11] 4,161,950
[45] Jul. 24, 1979

[54] ELECTROSURGICAL KNIFE

[75] Inventors: James D. Doss; Robert E. Cowan; Robert H. Newell; Charles W. McCabe, all of Los Alamos, N. Mex.

[73] Assignee: The United States of America as represented by the United States Department of Energy, Washington, D.C.

[21] Appl. No.: 601,113

[22] Filed: Aug. 1, 1975

[51] Int. Cl.² ............................................. A61N 3/04
[52] U.S. Cl. ........................ 128/303.14; 128/303.17; 219/10.81
[58] Field of Search ..................... 128/303.14, 303.17, 128/303.13; 219/10.81, 383, 384

[56] References Cited

U.S. PATENT DOCUMENTS

| 2,433,067 | 12/1947 | Russell | 219/10.81 X |
|---|---|---|---|
| 2,926,232 | 2/1960 | Gard | 219/10.81 X |
| 3,042,101 | 7/1962 | Spunt | 219/10.81 X |
| 3,460,539 | 8/1969 | Anhalt | 128/303.17 |
| 3,768,482 | 10/1973 | Shaw | 128/303.14 X |
| 3,826,263 | 7/1974 | Cage et al. | 128/303.14 X |
| 3,858,586 | 1/1975 | Lessen | 128/303.17 X |
| 3,934,115 | 1/1976 | Peterson | 128/303.14 X |
| 3,987,795 | 10/1976 | Morrison | 128/303.14 |
| 4,033,351 | 7/1977 | Hetzel | 128/303.14 |

*Primary Examiner*—Robert W. Michell
*Assistant Examiner*—Michael H. Thaler
*Attorney, Agent, or Firm*—Dean E. Carlson; Jerome B. Rockwood

[57] ABSTRACT

An electrosurgical knife blade of insulating material having a pair of electrodes adapted to be connected to a radiofrequency generator.

7 Claims, 5 Drawing Figures

ELECTROSURGICAL KNIFE

BACKGROUND OF THE INVENTION

Electrosurgical blades of the type employed by surgeons heretofore, have comprised essentially conventional surgical steel cutting tool, such as a scalpel, connected to a suitable radiofrequency source. In the prior art, the patient is placed in electrical contact with a "patient plate." The "patient plate" was connected to the ground terminal of the radiofrequency source, while the cutting blade was connected to the "hot" terminal of the radiofrequency source. Radiofrequency current flows from the edge of the cutting blade to the "patient plate" through the patient. Since the cutting blade is narrow and the "patient plate" is wide, the radiofrequency energy concentrates at the cutting edge of the knife, fanning out to the "patient plate" at the other side of the patient. Electrosurgical cutting blades cauterize small blood vessels as the blade penetrates tissue. However, in such prior art electrosurgery, patients have suffered from radiofrequency burns due to poor contact with the "patient plate." As will be apparent, if the radiofrequency energy is not spread over a large area as it leaves the patient's body entering the "patient plate," concentrations of radiofrequency energy due to lack of good overall contact may cause serious rf burns, since radiofrequency energy on the order of 100 W must be provided to enable sufficient energy concentration at the knife blade to be effective.

SUMMARY OF THE INVENTION

The electrical surgical blade of the present invention concentrates the radiofrequency field to the immediate vicinity of the blade. A blade of insulating material is provided, with rf electrodes closely adjacent to one another. As a result, much less radiofrequency power is required.

DESCRIPTION OF THE PREFERRED EMBODIMENT

Figure 1:
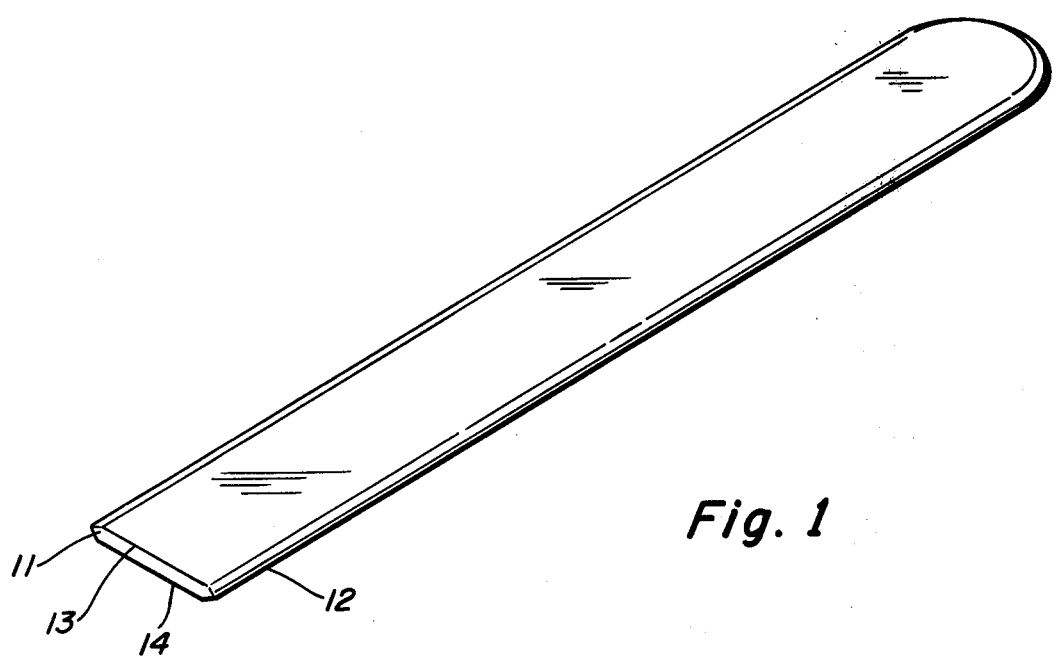
FIG. 1 is a perspective view of one embodiment of the electrosurgical knife of the present invention.
Figure 2:
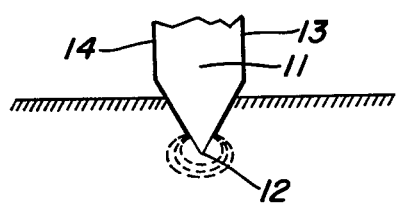
FIG. 2 illustrates the rf field produced by the knife of FIG. 1 in use.

Referring now to FIG. 1, the electrosurgical knife of the present invention comprises a blade 11 of a hard, strong insulating material, sharpened to provide a cutting edge 12 on either side. The insulating material blade 11 may have any desired shape as found in conventional steel surgical blades. Insulated blade 11 is preferably fabricated of a suitable ceramic material providing the necessary strength and capable of providing and maintaining a sharp edge. Each face of the insulating blade is coated with a thin layer of a suitable conductive material 13 and 14. Conductive coating 13 and 14 may conveniently be a layer of tungsten. The tungsten coating may be applied to the ceramic substrate in a variety of ways. At present, the preferred method is to brush-coat the substrate with a slurry of water and finely-divided tungsten powder. After drying, this coating is fired in a hydrogen atmosphere. The tungsten coatings on faces 13 and 14 are isolated from one another by the uncoated sharp edge 12 of the blade. As illustrated in FIG. 2 the radiofrequency field extends across the sharp edge of the blade 12 from electrode 13 to electrode 14.

Figures 3, 4:
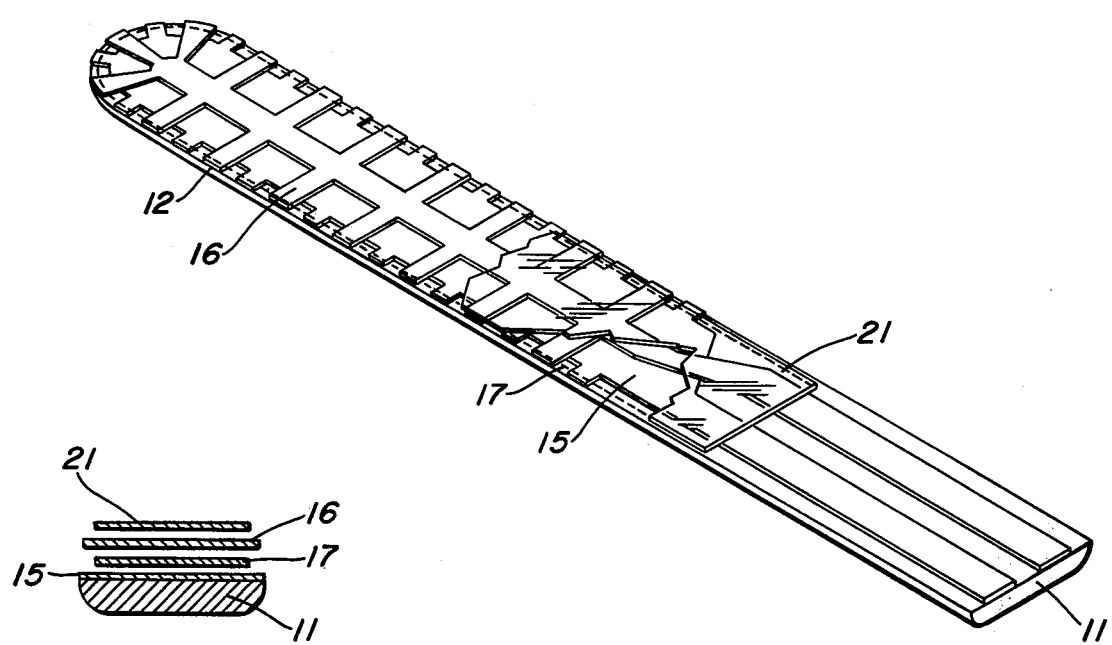
FIG. 3 illustrates another embodiment of the electrosurgical blade of the present invention.
FIG. 4 is an exploded cross section of the embodiment of FIG. 3.
Figure 5:
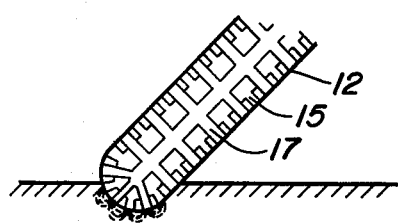
FIG. 5 illustrates the mode of operation of the embodiment of FIG. 3.

An alternative configuration of the electrosurgical blade of the present invention is illustrated in FIGS. 3, 4, and 5. In this embodiment the ceramic blade 11 may be substantially similar to that of FIG. 1 in plan, but having cutting edges adjacent to only one face. In this embodiment, the electrodes are placed on the same side of the blade as the cutting edge in the asymmetric cross section. A lower electrode 15, having a comb-shaped configuration, adheres directly to the ceramic substrate, with the teeth extended to the vicinity of cutting edge 12. An internal insulating layer 17 is placed on top of electrode 15. A second comb-like electrode 16 is placed on top of the insulating layer 17, with teeth extending to cutting edge 12 alternating with the teeth of electrode 15. The whole is covered with a surface insulating layer 21.

With the hereinabove disclosed configuration, the radiofrequency field runs parallel to the edge of the knife blade, in contrast with the arrangement of the embodiment of FIG. 1, wherein the radiofrequency field is directed across the edge of the blade. Conveniently, conventional printed circuit techniques may be employed for fabrication of the embodiment of the invention illustrated in FIG. 3. Exemplarily, the lower electrode 15 may be applied directly to the ceramic substrate 11 employing conventional printed circuit techniques. Insulating layer 17 may be applied in any convenient manner, well known to those skilled in the art. Upper electrode 16 is then applied to insulating layer 17. Finally surface insulator 21, preferably of a non-sticking material such as that known by the trade name "Teflon", may be applied in any convenient manner over the top of the upper printed circuit 16.

Other electrical circuit fabrication techniques may be employed. Exemplarily, the electrodes may be fabricated by vapor deposition, electroplating, electroless deposition, and other means known to the art.

In contrast with the relatively high power—i.e., 100 W—required with prior art electrosurgical blades, the short distance between the electrodes in the electrosurgical blade of the present invention allows the employment of rf generators having an output of only 2 W. As illustrated in FIGS. 2 and 5, the rf field is concentrated between the closely adjacent electrodes. Rf burns are eliminated, together with the causes, high rf power flowing through the patient's body to the "patient plate." There is no need to have the "patient plate" electrode make good rf contact over a large part of the patient's body.

The various features and advantages of the invention are thought to be clear from the foregoing description. However, various other features and advantages not specifically enumerated will undoubtedly occur to those versed in the art, as likewise will many variations and modifications of the preferred embodiment illustrated, all of which may be achieved without departing from the spirit and scope of the invention as defined by the following claims.

What we claim is:

1. A surgical implement adapted for use with a radio-frequency generator comprising:
   a blade of insulating material;
   a sharp cutting edge formed integrally of said insulating material on at least one edge of said blade, and, first and second conductive electrodes insulated from one another secured to said blade of insulating material adjacent said cutting edge.

2. In the surgical implement set forth in claim 1, a first electrode being placed on one side of said blade of insulating material and a second electrode being placed on the other side of said blade.

3. In the surgical implement set forth in claim 1, said first and second electrodes each having comb-shaped teeth, said teeth being interspersed between one another.

4. In the surgical implement set forth in claim 3, said first and second electrodes being secured on the same side of said blade, and an insulating layer interposed between said pair of electrodes.

5. A surgical implement adapted for use with a radio-frequency generator comprising:
   a blade of insulating material having a sharp cutting edge;
   a first conductive electrode secured on one side of said blade adjacent said cutting edge;
   a second conductive electrode secured on the other side of said blade adjacent said cutting edge, whereby said first and second electrodes are insulated from one another.

6. A surgical implement adapted for use with a radio-frequency generator comprising:
   a blade of insulating material having a sharp cutting edge;
   a first electrode on said blade secured to said blade adjacent said cutting edge; a second electrode secured substantially overlying said first electrode; and,
   means insulating said first and second electrodes from one another.

7. In the surgical implement set forth in claim 6:
   said first electrode having an array of comb-shaped teeth adjacent said cutting edge; and,
   said second electrode having an array of comb-shaped teeth interspersed between said teeth on said first electrode.

* * * * *